(12) United States Patent
Santo et al.

(10) Patent No.: US 7,615,239 B2
(45) Date of Patent: Nov. 10, 2009

(54) TEA FOR TREATING DERMATITIS COMPRISING HERBAL EXTRACTS

(75) Inventors: Tetsuo Santo, 360-130, Hinashicho, Hamada-Shi, Shimane 697-1322 (JP); Songhua Li, Izumo (JP); Ruwei Wang, Zhejiangsheng (CN); Sumio Iwasaki, Izumo (JP)

(73) Assignee: Tetsuo Santo, Shimane (JP)

( * ) Notice: Subject to any disclaimer, the term of this patent is extended or adjusted under 35 U.S.C. 154(b) by 525 days.

(21) Appl. No.: 10/511,024

(22) PCT Filed: Apr. 15, 2002

(86) PCT No.: PCT/JP02/03749

§ 371 (c)(1), (2), (4) Date: Apr. 6, 2005

(87) PCT Pub. No.: WO03/086434

PCT Pub. Date: Oct. 23, 2003

(65) Prior Publication Data

US 2005/0186293 A1     Aug. 25, 2005

(51) Int. Cl.
*A61K 36/539* (2006.01)
*A61K 36/534* (2006.01)
*A61K 36/20* (2006.01)
*A61K 36/40* (2006.01)
*A61K 36/44* (2006.01)
*A61K 36/49* (2006.01)
*A61K 36/52* (2006.01)
*A61K 36/76* (2006.01)
*A61K 36/63* (2006.01)

(52) U.S. Cl. ............... 424/725; 424/736; 424/747; 424/741; 424/757; 424/771; 424/774

(58) Field of Classification Search ............... None
See application file for complete search history.

(56) References Cited

U.S. PATENT DOCUMENTS 5,466,443 A * 11/1995 Ho et al. ............... 424/70.6

FOREIGN PATENT DOCUMENTS

| CN | 1077896 A | * | 3/1993 |
| CN | 1095291 A | * | 11/1994 |
| CN | 1110163 A | * | 10/1995 |
| CN | 1134837 A | * | 11/1996 |
| CN | 1146353 A | * | 4/1997 |
| CN | 1189343 A | * | 5/1998 |
| CN | 1195537 A | * | 10/1998 |
| CN | 1252296 A | * | 10/2000 |
| CN | 1324646 A | * | 5/2001 |
| DE | 19838462 | | 3/2000 |
| JP | 61-50921 | | 3/1986 |
| JP | 3-27318 | | 2/1991 |
| JP | 4-356423 | | 12/1992 |
| JP | 6-9371 | | 1/1994 |
| JP | 06-166629 | | 6/1994 |
| JP | 6-321795 | | 11/1994 |
| JP | 7-10764 | | 1/1995 |
| JP | 08-301779 | | 11/1996 |
| JP | 9-2938 | | 1/1997 |
| JP | 9-108111 | | 4/1997 |
| JP | 09-227398 | | 9/1997 |
| JP | 10-236944 | | 9/1998 |
| JP | 11-199500 | | 7/1999 |
| JP | 2000-23649 | | 1/2000 |
| JP | 2000-44481 | | 2/2000 |
| JP | 2000-103718 | | 4/2000 |
| JP | 2000-154151 | | 6/2000 |
| JP | 2000-169383 | | 6/2000 |
| JP | 2000-212059 | | 8/2000 |

(Continued)

OTHER PUBLICATIONS

F. Diel et al., "Tea of Isatis tinctoria (woad) responses by allergic patients in vivo and in vitro" Aktuelle Emahrungsmedizin, ISSN 0341-0501, 1992, vol. 17, No. 1, pp. 34-36.
Jai Tung Huang et al., "New Iridoid from Oldenlandia Diffusa ROXB" Archiv der Pharmazie (Germany, F.R.), ISSN 0365-6233, 1981, vol. 314, No. 10, pp. 831-836.

(Continued)

*Primary Examiner*—Christopher R Tate
*Assistant Examiner*—Amy L Clark
(74) *Attorney, Agent, or Firm*—J.C. Patents

(57) ABSTRACT

Technical Field: Tea
Technical Problem: To provide a drinkable tea having a high therapeutic effect against atopic dermatitis.
Means for Solving: It is characterized in that it contains extracts drawn from one, two or more medicinal herbs selected from the group consisting of Lightyellow *Sophora* Root, *Isatis* Leaf, and *Terminalia* Fruit. Atopic dermatitis can be cured by improving allergic constitution from the inside of body owing to antibacterial effect and antiviral effect of Lightyellow *Sophora* Root, *Isatis* Leaf and *Terminalia* Fruit, antiallergic effect of Lightyellow *Sophora* Root and *Isatis* Leaf, and intestinal mucosal protecting effect of *Terminalia* Fruit, or by a synergistic effect of them.

In addition, the pharmacological effect in said extracts drawn from plants is enhanced, a pharmacological effects lacking in said extracts drawn from plants are added, or easiness of drinking the tea as a drinkable drug is improved and thus the therapeutic effect is improved by adding one, two or more auxiliary materials selected from the group of Japanese *Angelica* Root, *Oldenlandia diffusa*, *Smilax Glarba*, Dried Tangerine Peel, Wild *Chrysanthemum* Flower, *Corydalis*, Peppermint, Baikal Skullcap, *Lithospermum*, *Kudingcha*, Smartweed, and Licorice to the extracts drawn from plants.
Principal Use: It is used for the therapy of dermatitis, particularly of atopic dermatitis.

4 Claims, 7 Drawing Sheets

FOREIGN PATENT DOCUMENTS

| | | |
|---|---|---|
| JP | 2001-64192 | 3/2001 |
| JP | 2001-81037 | 3/2001 |
| JP | 2001-226213 | 8/2001 |
| JP | 2001-233756 | 8/2001 |
| JP | 2002-20225 | 1/2002 |
| JP | 2002-47193 | 2/2002 |
| JP | 2000-103718 | 10/2005 |
| SU | 917839 B * | 4/1982 |
| SU | 1793927 A3 * | 2/1993 |
| WO | WO 99/22749 | 5/1999 |

* cited by examiner (A)

(B)

(A)

(B)

(A)

(B)

(A)

(B)

(A)

(B)

(A)

(B)

(A)

(B)

TEA FOR TREATING DERMATITIS COMPRISING HERBAL EXTRACTS

TECHNICAL FIELD

The present invention relates to a drinkable tea for therapy of dermatitis, and relates to a drinkable tea for therapy of dermatitis which is suitable to treat dermatitis by improvement of physical constitution of a patient having various dermatitis including eczema, particularly, for example, atopic dermatitis.

BACKGROUND ART

Patients having dermatitis, particularly atopic dermatitis, have suddenly increased in recent years. While the grounds for the sudden increase of patients having atopic dermatitis has not been sufficiently clarified, it is considered that the grounds are classified into three large groups. The first ground is a change in the eating habit. That is, by an increase in consumption of flesh and meat as well as dairy product such as butter, cheese and the like, changed from the conventional vegetable-centered diet, it is considered that the physical constitution itself has been changed. The second ground is a change in the living environment. That is, by a change from the conventional houses using wood, plaster, paper, rush-mat and the like to houses using various synthetic building materials, chemically synthesized size, chemical mat and the like, it is considered that various chemical substances contained in these building materials are released in the living environment resulting in the change in the physical constitution. In addition, irritation on the skin may be increased by a change from the conventional clothes made of natural material fibers such as wool, cotton and the like to clothes made of various chemical fibers resulting in increase of irritation onto the skin, and a changing from washing with soaps to washing with synthetic detergents and dry-cleaning, and a use of shampoos, rinses, hair conditioners may also be grounds. As the third ground, it is considered that a level down in immunity is caused by speed-up in the living rhythm and raised level of work proceeded in all the aspect, resulting in exposure of infants and adults to excess stress.

Atopic dermatitis is a disease occurred to the children whose resistance power is poor and having an age from two- or three-months old to about ten years old. The patients are accompanied by intense itch with wetting and erosion. The itch is given a mental pain to the patients and aggravated symptoms by scratching. Particularly, in the case of infant patient, it is painful not only for the patients themselves but also for the parents and near relations.

Although various countermeasures have been examined and practiced for the prophylaxis or therapy of this atopic dermatitis, most of them are countermeasures belonging to the symptomatic therapy; particularly known are antihistaminic agents, antiallergic agents, antiphlogistic agents, steroidal agents and the like for the symptomatic therapy of western medicine, but all of them have been unsatisfactory in pharmacological effect and side effects.

For example, although antihistaminic agents and antiallergic agents have an action of suppressing itch, they have problems in the duration of effect and antiphlogistic effect, and are problematic in long-term administration for chronic itching because sometimes they bring about troubles in the daily life due to symptoms such as weariness, sleepiness and the like caused by administration.

Although steroidal agents have generally a high pharmacological effect, they are fundamentally drugs for suppressing symptoms, and sometimes the cure cannot be attained even by a long-term administration of steroidal agents; they are problematic because of their strong drug-characteristic side effects; for example, sometimes they cause dermatrophia in which the skin becomes thin like a flimsy, capillarectasia in which capillary blood vessel in the skin rises forming redskin, and various infections such as fungal infection, folliculitis (pimple), herpes and the like due to decrease in the immune power. Additionally, when a very large amount of a very strong steroidal agent is used within a short period, sometimes functional disorder of adrenal grand, shock and the like occurs. In another case, when use of steroidal agent is suddenly discontinued after a long-term use, problems arises that the daily life become difficult by a revival of symptoms suppressed before by the steroidal agent and a rebound phenomenon (jump back) in which symptoms such as itching, redness, swelling and the like increases more than before.

In addition, based on the fact that *Staphyllocaccus aureus* and others were found in the diseased part of atopic dermatitis, application of Isodine, a disinfectant agent, has been practiced in some cases. Indeed the effect of application of Isodine has been confirmed in a skin on which bacteria is abundant, isodine is effective only to bacteria floating on the surface of skin, and has no effect against bacteria within a biological membrane or bacteria invaded deeply in the skin. Not only that, Isodine is liable to cause a rash, and when once a rash is caused, the reaction is repeated and sometimes an ulcer is formed on the skin or a reaction such as shock or the like is caused. Moreover, sometimes hypothyroidism is induced.

From a similar viewpoint against bacteria, sometimes upper acidic water is used, but problems similar to those in Isodine arise.

In addition to the above-described countermeasures based on western medicine, treatment by Sino-Japanese medicament have also been practiced. For example, respective crude drug ingredients of *Rhizoma coptidis* detoxication soup and Heat-clearing and wind-dispelling powder as therapeutic agents for atopic dermatitis are Baikal skullcap, Coptis Root, Gardenia Fruit, Amur Cork Tree and Japanese *Angelicae* Root, Chinese Fox-Glove Root, Gypsum, Saposhnikoviae Radix, Great Burdock Achene, Akebiae Stem, *Anemarrhena rhizome*, Sesame, *Cryptotympana atrata*, Lightyellow *Sophora* Root; since they belong to anti-itching agents for suppressing itch or blood-activation agents for stopping pain by improving blood circulation and therefore respective drugs belong to the symptomatic therapy dealing with individual symptoms, these medicaments cannot be said to be medicaments for fundamental cure.

In addition, although drugs for paint such as ointments containing Sino-Japanese drugs have been prepared, these belong also to so-called symptomatic therapy and therefore are far from the fundamental cure by improvement of physical constitution.

Moreover, while the activity is mild, Sino-Japanese drugs with a purpose of suppressing the aforementioned side effects have been proposed. For example, Japanese Patent Publication JP-A-6-166629 has proposed an agent for improving atopic dermatitis formed by mixing Potent Bupleuri Decoction and *Angelica* peony powder. Indeed side effects are suppressed in these agents for improving atopic dermatitis, there is a problem that its anti-itching effect is not sufficient.

Beside, Japanese Patent Publication JP-A-8-301779 has proposed an external drug for atopic dermatitis containing as an active ingredient an extract solution from one, two or more plants selected from the group consisting of Linden, Lemonbalm, Fenugreek, Borage, *Ligusticum chuanxiong* Hort, Pink Pyrola, Willowleaf Swallowwort Rhizome, *Chlerodendron cyrtophyllum*, and Clinopodium chinese.

However, while the external drugs for atopic dermatits exerts some anti-itching effect and disease-improving effect by applying it onto the diseased part, it is an agent for suppressing a symptom acting on the symptom appeared on the outside surface of body, and not an agent for fundamental cure onto the basis for the symptom, there was a problem that the itching symptom revived when its application was discontinued.

Therefore, the purpose of the present invention is to provides a drinkable tea for therapy of dermatitis which enables therapy of dermatitis, particularly atopic dermatitis, by improvement of physical constitution itself of a patient having dermatitis, particularly atopic dermatitis, by drinking, and not an external preparation like conventional ones as described above.

DISCLOSURE OF THE INVENTION

The drinkable tea for therapy of dermatitis according to the present invention is characterized in that it contains extracts drawn from one, two or more medicinal herbs selected from the group consisting of Lightyellow *Sophora* Root, *Isatis* Leaf, and *Terminalia* Fruit.

The families and tastes, main components and principal activities of the plants as raw materials for the above-mentioned respective extracts drawn from plants are described briefly in the following:

(1) Lightyellow *Sophora* Root (Kujin) (*Sophora flavescens* Ait.)
Family and taste: *Leguminosae* plant, bitter.
Main components: Matrine, Kurarinone
Principal activities: Antibacterial, Antiviral, Antiallerigic (2) *Isatis* Leaf (Taiseiyou) (*Isatis tinctoria* L.)
Family and taste: *Acantaceae* plant, bitter.
Main components: Indigo, Indirubin, Indican, Trace Element
Principal activities: Antibacterial, Antiviral, Antialleric In addition, *Isatis* Leafs prepared from *Baphicacanthus cusia* Bremek, *Isatis Indigotica* Fort, *Polygonum tinctorium* Ait., *Clerodendron cyrtophyllum* Turcz and the like can be used.

(3) *Terminalia* Fruit (Kashi) (*Terminalia chebula* Retz.)
Family and taste: *Combretaceae* plant, bitter and acid.
Main components: Tannin, Chebulic acid, Chebulagic acid
Principal activities: Antibacterial, Antiviral, Intestinal mucosa protecting. Japanese *Angelicae* Root (*Angelicae sinensis* (Olive) Diels.)

According to the above described drinkable tea for therapy of dermatitis, allergic constitution can be improved from the inside of body through a protection of roughness of gastrointestinal mucosa by extracts drawn from medicinal herbs, together with a depression effect against allergens, and thus atopic dermatitis can be cured, owing to antibacterial effect of *Terminalia* Fruit, or by a synergistic effect of them.

This drinkable tea may be taken in the liquid form of extracts itself drawn from medicinal herbs, or in a once pulverized or granulated form together with water or hot water. When it is in a powdery or granular form, the drinkable tea may be contained in a cavity of mouth before taking hot water or water like the conventional powdery or granular drinkable tea, or it may be taken after once dissolving in hot water or water.

The above mentioned term "dermatitis" is not limited to atopic dermatitis but includes various dermatitis such as xeroderma dermatitis, autosensitization dermatitis, dermatitis seborrhoica, contact dermatitis, diaper dermatitis and the like, and various eczemas such as nummular eczema, hand eczema (including housewife eczema), infantile eczema, impetiginous eczema, xerosis eczema, acute eczema, chronic eczema, miliaria eczema, heteromiliaria eczema and the like.

The invention is also characterized in addition of an auxiliary material to the above described extracts drawn from medicinal herbs.

As the auxiliary material, materials having various auxiliary activities can be adopted, including one for assistance and enhancements of pharmocological effects of aforementioned extracts drawn from plants, one for addition of one, two or more pharmocological effects, for example, acceleration of blood-circulation, improvement of anemia, regulation of immunity power, antiphlogistic action, antidotal action, inhibition of tumor, enhancement of immunity power, acceleration of digestion, anti-emetic action, expectorant action, sedative action, analgesic action, anti-itching action, control of intestinal function, pyretosis, antifungal action, hypolipemic action and the like, which are lacking in aforementioned extracts drawn from plants, or one for improvement of easiness of drinking the tea as a drinkable drug by conferring sweetness or cold feeling.

According to the above drinkable tea for therapy of dermatitis, with the use of the auxiliary material, the therapeutic effect as a drinkable drug is promoted by assisting or enhancing the pharmacological effects of the extracts drawn from plants, adding a pharmacological effects lacking in the extracts drawn from plants, or improving easiness as a drinkable drug, and drinking can be continued for a period needed in therapy without difficulty by removing resistance against drinking.

The invention is also characterized in that above described auxiliary material contains extracts drawn from one, two or more medicinal herbs selected from the group of Japanese *Angelica* Root, *Oldenlandia diffusa*, *Smilax Glarba*, Dried Tangerine Peel, Wild Chrysanthemun Flower, *Corydalis*, Peppermint, Baikal Skullcap, *Lithosperum*, *Kudingcha*, Smartweed, and Licorice.

The families and tastes, main components and principal activities of the medicinal herbs as auxiliary material are described briefly in the following:

(1) Japanese *Angelicae* Root (Touki) (*Angelica sinensis* (Olive) Diels.)
Family and taste: Umbelliferae plant, sweet and salty.
Main components: Volatile oil, Ferulic acid, Vitamin E, Vitamin A, Vitamin $B_{12}$
Principal activities: Blood-circulation accelerating, Anemia improving, Immunity regulating, Antiallergic (2) *Oldenlandia diffusa* (Byakkajazetusou) (*Oldenlandia diffusa* Roxb.)
Family and taste: Rubiaceae plant, sweet.
Main components: Flavonoids
Principal activities: Antibacterial, Antiviral, Antiphlogistic, Antidotal, Tumor inhibiting, Immunity enhancing (3) *smilax glabra* (Topukurei) (*Smilax glabra* Roxb.)
Family and taste: Liliaceae plant, sweet.
Main components: Biological alkali
Principal activities: Antiphlogistic, Antiallergic, Antidotal (4) Dried Tangerine Peel (Chinpi) (*Citrus reticulata* Blanco.)
Family and taste: Rutaceae plant, sweet and salty.
main components: Volatile oil, Vitamin B, Vitamin C
Principal activities: Digestion accelerating, Anti-emetic, Expectorant (5) Wild Chrysanthemum Flower (Nogikuka) (*Chrysanthemum indicum* L.)
Family and taste: Compositae plant, bitter.

Main components: Volatile oil, Trace elements
Principal activities: Antibacterial, Antiphlogostic
  (6) *Corydalis* (Genko) (*Corydalis bulbosa* DC.)
Family and taste: Papaveraceae plant, bitter.
Main components: Containing 15 alkaloids. Relatively important ones being Colydaline B, Colydaline L, Colydaline A
Principal activities: Blood-circulation improving, Sedative, Analgesic
  (7) Peppermint (Hakka) (*Mentha arvensis* L.)
Family and taste: Labliatae plant, salty.
Main components: Volatile oil, Manthol, Menihone
Principal activities: Antiphlogostic, Anti-itching, Intestinal function comtrolling
  (8) Baikal Skullcap (Ougon) (*Scutellaria baicalensis* Georgi.)
Family and taste: Labliatae plant, bitter.
Main components: Baicalin, Baicalein
Principal activities: Antibacterial, Antiviral, Antiallergic
  (9) *Lithospermum* (Sisou) (*Lithospermum erythrorhizon* Sieb. et Zucc.)
Family and taste: Boraginaceae plant, sweet.
Main components: Acetylshikonin, Shironin
Principal activities: Antipyretic, Antidotal, Antifungal, Antiviral
  (10) *Kudingcha* (Kuteicha) (*Kudingcha*)
Family and taste: Birdlime plant, sweet and salty.
Main components: Ulsolic acid, B-Amyrin, Lupeol
Principal activities: Digestion accelerating, Hypolimetic, Antiphlogostic
  (11) Smartweed (Kojou) (*Polygonum cuspidatum* Sieb. et Zucc.)
Family and taste: *Polygonaceae* plant (Smartweed), bitter.
Main components: Glucosides, Flabonoids
Principal activities: Antibacterial, Antiviral, Antiallergic
  (12) Licorice (Kanzou) (*Glycyrrhiza uralensis* Fisch.)
Family and taste: Legminosae plant
Main components: Glycyrrhetic acid, Flabonoids
Principal activities: Antiallergic, Antiphlogostic According to the above described drinkable tea for therapy of dermatitis, the pharmacological effects of the extracts drawn from plants consisting of Lightyellow *Sophora* Root, *Isatis* Leaf, and *Terminalia* Fruit can be enhanced by the principal activities of respective auxiliary materials. For example, the effects can be assisted and enhanced respectively by *Oldenlandia diffusa*, Wild Crysanthemum Flower, Baikal Skullcap and Smartweed for the antibacterial effect, and by *Oldenlandia diffusa*, Baikal Skullcap, *Lithospermum* and Smartweed for the antiviral effect, and moreover, by *smilax glabra*, Baikal Skullcap, Smartweed and Licorice for the allergic effect.

In addition, pharmacologocal effects lacking in the extracts drawn from plants consisting of Lightyellow *Sophora* Root, *Isatis* Leaf, and *Terminalia* Fruit can be added. For example, blood-circulation accelerating, anemia improving and immunity regulating effects of Japanese *Angelica* Root, antidotal, tumor inhibiting and immunity enhancing effects *Oldenlandia deffusa*, antiphlogistic and antidotal effects of *smilax glabra*, digestion accelerating, anti-emetic and expectorant effects of Dried Tangerine Peel, antiphlogistic effect of Wild Chrysanthemum Flower, blood-circulation accelerating, sedative and analgesic effects of *Corydalis*, antiphlogistic, anti-itching and intestine regulating effects of Peppermint, antidotal, antipyretic and antifungal effects of *Lithospermum*, antiphlogistic and digestion accelerating effects of *Kudingcha*, antiphlogistic effect of Licorice and so on can be added.

Additionally, easiness of drinking can be improved by conferring sweetness and cold feeling lacking in the extracts drawn from plants consisting of Lightyellow *Sophora* Root, *Isatis* Leaf, and *Terminalia* Fruit resulting in a drinkable tea having higher effects. For example, sweetness can be added by *Olenlandia diffusa*, *smilax glabra*, *Lithospermum*, Licorece and so on, and cold feeling can be added by Peppermint.

The invention is also characterized in that said extracts drawn from medicinal herbs contain Lightyellow *Sophora* Root, *Isatis* Leaf, and *Terminalia* Fruit and the weight ratios of extracts drawn from Lightyellow *Sophora* Root, *Isatis* Leaf, and *Terminalia* Fruit are 41 to 50% of Lightyellow *Sophora* Root, 41 to 50% of *Isatis* Leaf, and 8 to 10% of *Terminalia* Fruit.

According to the above described drinkable tea for therapy of dermatitis, the respective ingredients from Lightyellow *Sophora* Root, *Isatis* Leaf, and *Terminalia* Fruit are contained with a good balance, and a drinkable tea having a high therapeutic effect can be obtained. When Lightyellow *Sophora* Root is less than 45%, appearance of therapeutic effect is slow or no improving effect appears; when it exceeds 50%, there is a fear that a side effect in which skin become red and swelled or the symptom become worse. When *Isatis* Leaf is less than 45%, appearance of therapeutic effect is slow or no improving effect appears; when it exceeds 50%, there is a fear that a side effect in which skin become red and swelled or the symptom become worse. When *Terminalia* Fruit is less than 8%, appearance of therapeutic effect is slow or no improving effect appears; when it exceeds 10%, there is a fear that a side effect in which skin become red and swelled or the symptom become worse.

The invention is further characterized in that the weight ratio of saod extracts drawn from medicinal herbs: Lightyellow *Sophora* Root, *Isatis* Leaf, and *Terminalia* Fruit and the auxiliary material in said drinkable tea is 18 to 25%:75 to 82%.

According to the above described drinkable tea for therapy of dermatitis, the extracts ingredients drawn from three medicinal herbs: Lightyellow *Sophora* Root, *Isatis* Leaf, and *Terminalia* Fruit and the ingredients of auxiliary materials are contained with a good balance, and a high therapeutic effect can be obtained. When extract ingredients drawn from three medicinal herbs: Lightyellow *Sophora* Root, *Isatis* Leaf and *Terminalia* Fruit are less than 18%, appearance of therapeutic effect is slow or no improving effect appears; when it exceeds 25%, there is a fear that a side effect in which skin become red and swelled or the symptom become worse. In addition, when auxiliary materials are less than 75%, appearance of therapeutic effect is slow or no improving effect appears; when it exceeds 82%, there is a fear that a side effect in which skin become red and swelled or the symptom become worse.

The invention is further characterized in that said drinkable tea is in the form of liquid.

According to the above described drinkable tea for therapy of dermatitis, it is easily drunk because it is in the form of liquid. Beside, the term "liquid" refers to a product dissolved in water or hot water in principle, but intended to include a product in another liquid such as milk, juice or the like, according to preference of patient or particularly in the case of infant and the like.

The invention is further characterized in that said drinkable tea is in the form of powder or granule.

According to the above described drinkable tea for therapy of dermatitis, drinking can be attained either by containing the drinkable tea in the form of powder or granule in mouth and taking water or hot water in the mouth, or by dissolving the drinkable tea in water or hot water. Since it is in the form of powder or granule, it has a good preserving property, and it is less bulky as compared with liquid product; therefore, space for storage is small and deterioration is unlikely; particularly, it has an advantage that is easily carried in the case of travel or the like.

The invention is further characterized in that the weights of extract ingredients drawn from respective medicinal herbs per g of a drinkable tea are: Lightyellow *Sophora* Root, 0.09 to 0.11 g; *Isatis* Leaf, 0.09 to 0.11 g; and *Terminalia* Fruit, 0.018 to 0.022 g; and the weights of said auxiliary material are: Japanese *Angelica* Root, 0.045 to 0.055 g; *Oldenlandia diffusa*, 0.09 to 0.11 g; *Smilax Glabra*, 0.108 to 0.132 g; Dried Tangerine Peel, 0.045 to 0.055 g; Wild Chrysanthemum Flower, 0.09 to 0.11 g; *Corydalis*, 0.018 to 0.022 g; Peppermint, 0.09 to 0.11 g; Baikal Skullcap, 0.045 to 0.055 g; *Lithospermum*, 0.09 to 0.11 g; *Kudingcha*, 0.045 to 0.055 g; Smartweed, 0.09 to 0.11 g; and Licorice, 0.0273 to 0.033 g.

According to the above described drinkable tea for therapy of dermatitis, the respective ingredients are contained with a good balance, and a high therapeutic effect can be obtained. When respective ingredients drawn from medicinal herbs are less that the lower limit of the above range, appearance of therapeutic effect is low or no improving effect appears; when it exceeds the upper limit of the above range, there is a fear that a side effect in which skin become red and swelled or the symptom become worse occurs.

The invention is further characterized in that the weights of extract ingredients drawn from respective medicinal herbs per g of a drinkable tea are: Lightyellow *Sophora* Root, 0.1 g; *Isatis* Leaf, 0.1 g; and *Terminalia* Fruit, 0.02 g; and the weights of said auxiliary materials are: Japanese *Angelica* Root, 0.05 g; *Oldenlandia diffusa*, 0.1 g; *Smilax Glabra*, 0.12 g; Dried Tangerine Peel, 0.05 g; Wild Chrysanthemum Flower, 0.1 g; *Corydalis*, 0.02 g; Peppermint, 0.01 g; Baikal Skullcap, 0.05 g; *Lithospermum*, 0.1 g; *Kudingcha*, 0.05 g; Smartweed, 0.1 g; and Licorice, 0.03 g.

According to the above described drinkable tea for therapy of dermatitis, the respective ingredients are contained with a best balance, and a very high therapeutic effect can be obtained.

The invention is further characterized in that 1 g of said drinkable tea in the form of powder or granule is contained in a unit package.

According to the above described drinkable tea for therapy of dermatitis, the amount for once drinking can be exactly taken, and not only that, particularly, it has an advantage that it is easily carried and taken in the case of travel or the like.

Since drinkable tea for therapy of dermatitis according to the invention is characterized in that it contains extracts drawn from one, two or more plants selected from the group consisting of Lightyellow *Sophora* Root, *Isatis* Leaf, and *Terminalia* Fruit, dermatitis including atopic dermatitis is cured improving physical constitution from the inside of body owing to antibacterial effect and antiviral effect of Lightyellow *Sophora* Root, *Isatis* Leaf and *Terminalia* Fruit, antiallergic effect of Lightyellow *Sophora* Root and *Isatis* Leaf, and intestinal mucosal protecting effect of *Terminalia* Fruit, or by a synergistic effect of them; a higher therapeutic effect against atopic dermatitis can be obtained as compared with conventional antihistamines, antiallergic agents, antiphlogistic agents and steroidal agents, and not only that, it has no irritation and side effect, and additionally, avoidance of recurrence can be attained when drinking is discontinued after improvement of the physical constitution.

(B) is a photograph showing the backsides of both hands after treatment.

Figure 2:
Figure 2:

FIG. 2 (A) is a photograph showing the face when the patient in CASE 2 according to the invention has visited a doctor for initial consultation.

(B) is a photograph showing the face after treatment.

Figure 3:
Figure 3:

FIG. 3 (A) is a photograph showing the backside of right hand when the patient in CASE 2 according to the invention has visited a doctor for initial consultation.

(B) is a photograph showing the backside of right hand after treatment.

Figure 4:
Figure 4:

FIG. 4 (A) is a photograph showing the face when the patient in CASE 3 according to the invention has visited a doctor for initial consultation.

(B) is a photograph showing face after treatment.

Figure 5:
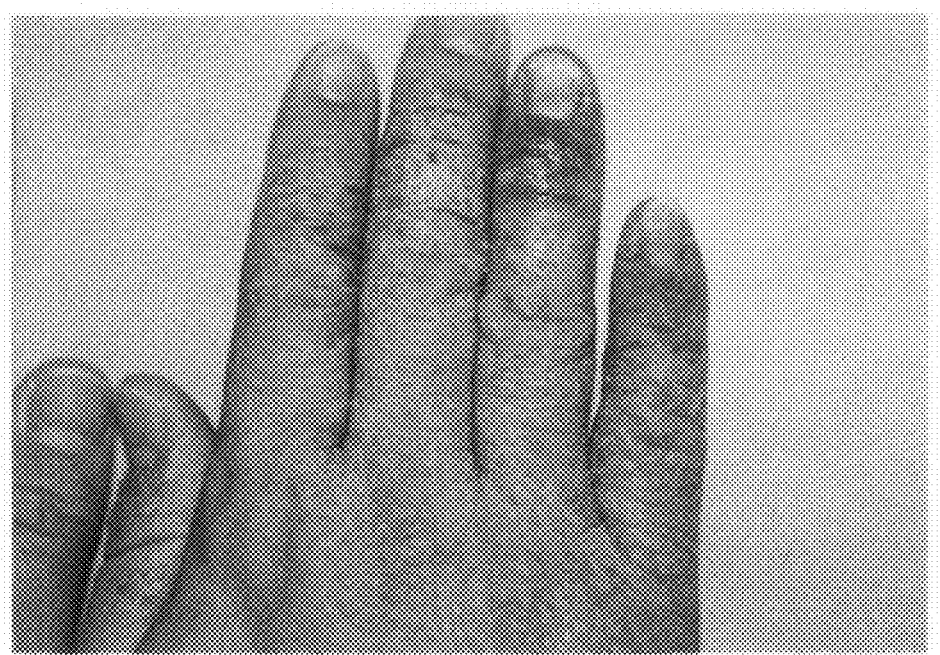
Figure 5:
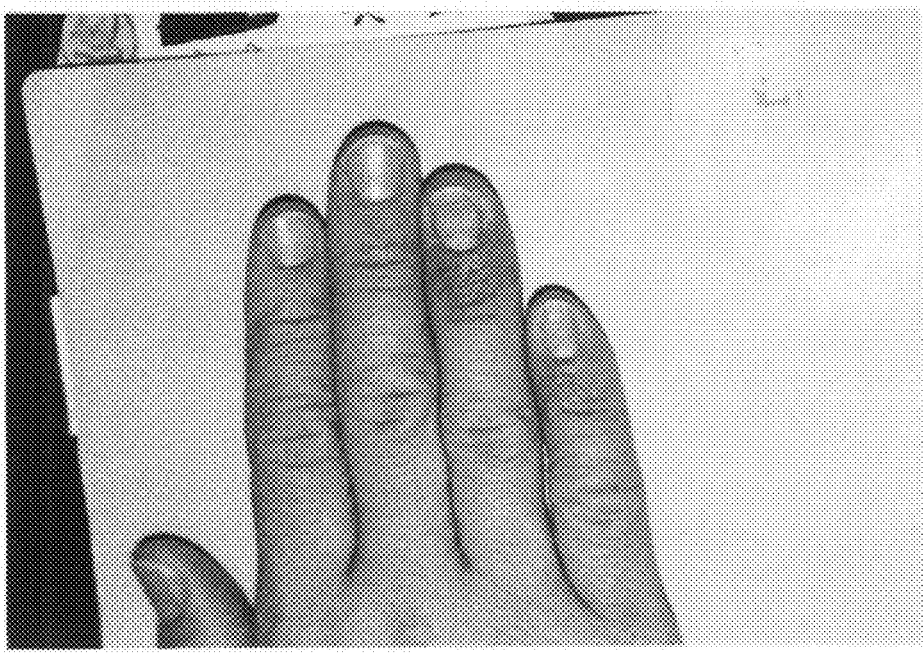

FIG. 5 (A) is a photograph showing the fingers of right hand when the patient in CASE 4 according to the invention has visited a doctor for initial consultation.

(B) is a photograph showing the fingers of right hand after treatment.

Figure 6:
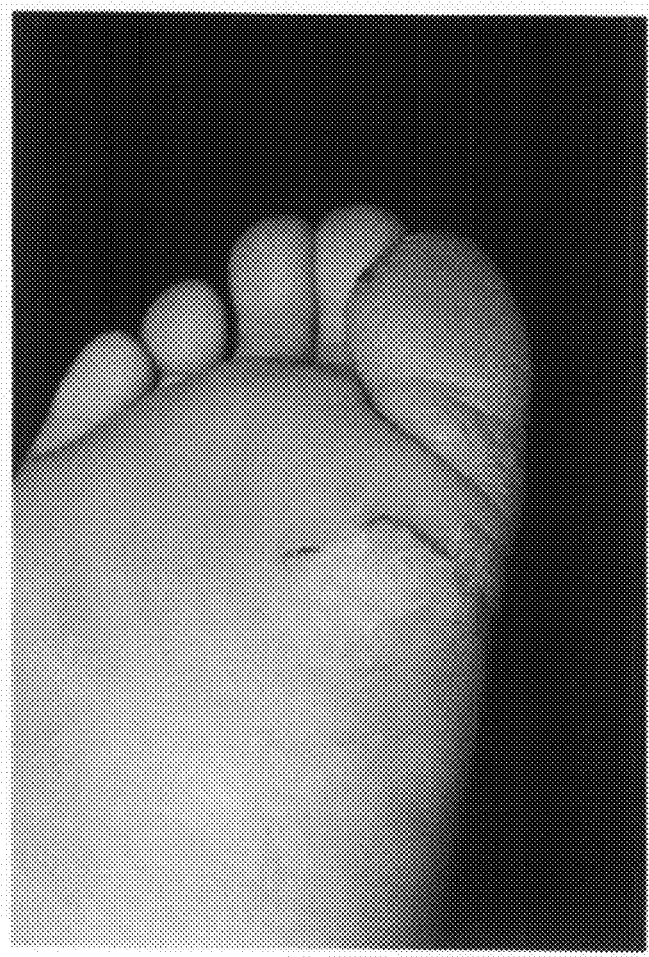
Figure 6:
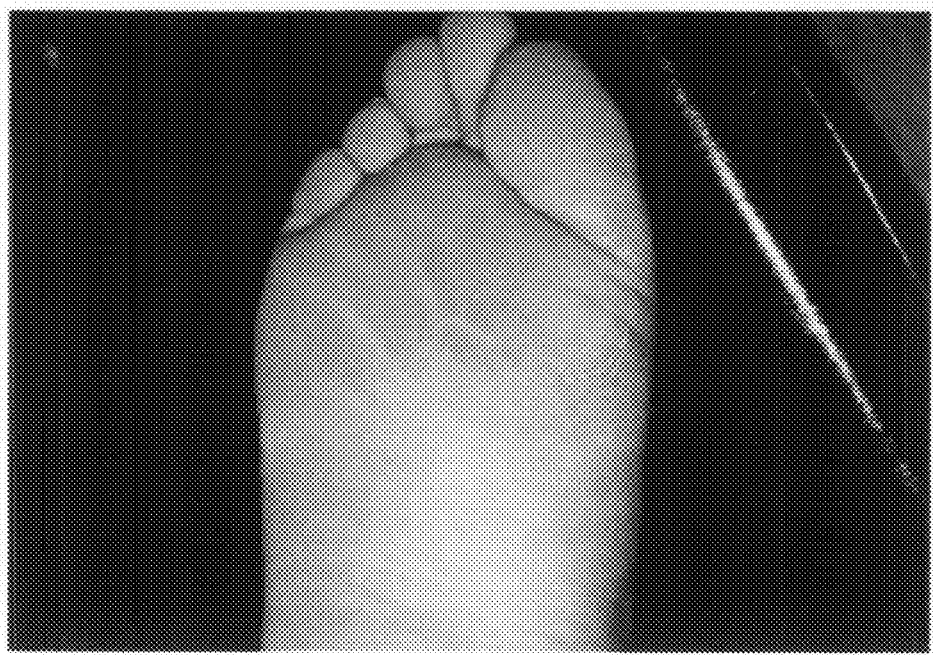

FIG. 6 (A) is a photograph showing the sole of right foot when patient in CASE 5 according to the invention has visited a doctor for initial consultation.

(B) is a diagram showing the sole of right foot after treatment.

Figure 7:
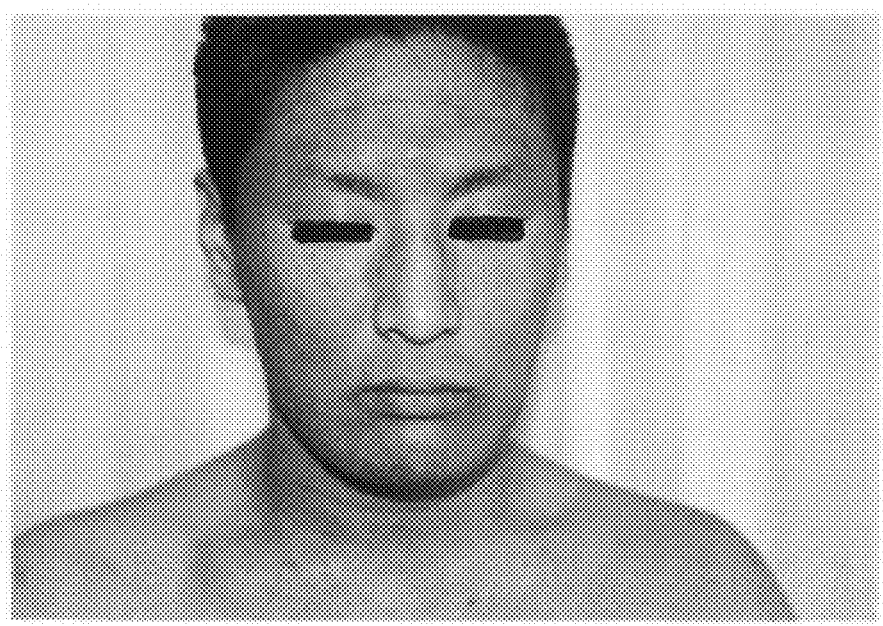
Figure 7:
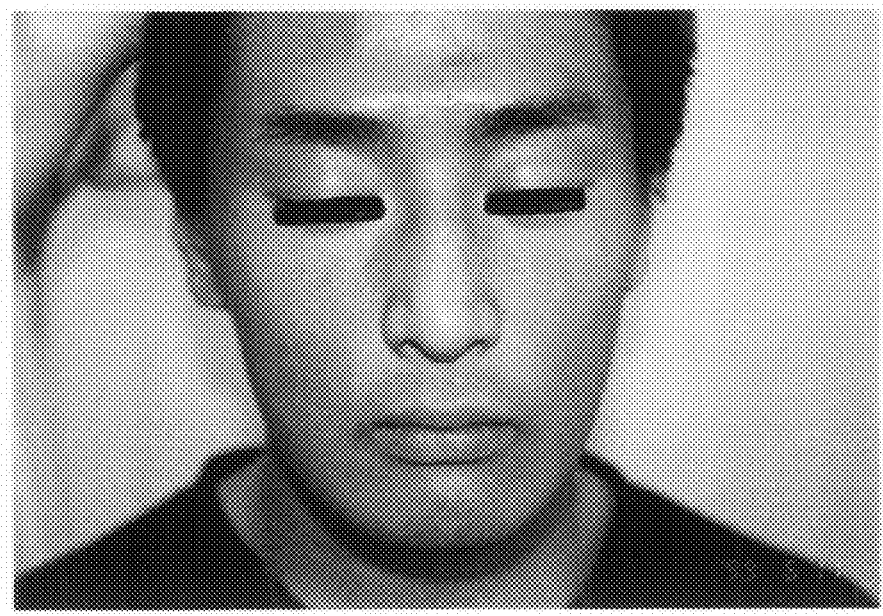

FIG. 7 (A) is a photograph showing the face when the patient in CASE 6 according to the invention has visited a doctor for initial consultation.

(B) is a photograph showing the face after treatment.

BEST MODE FOR CARRYING OUT THE INVENTION

When a patient of atopic dermatitis drank a drinkable tea in which the weights of extracts ingredients drawn from respective medical herbs per g of a drinkable tea in the form of powders or granules are: Lightyellow *Sophora* Root, 0.1 g; *Isatis* Leaf, 0.1 g; and *Terminalia* Fruit, 0.02 g; Japanese *Angelica* Root, 0.05 g; *Oldenlandia diffusa*, 0.1 g; *Smilax Glabra*, 0.12 g; Dried Tangerine Peel, 0.05 g; Wild Chrysanthemum Flower, 0.1 g; *Corydalis*, 0.02 g; Peppermint, 0.01 g; Baikal Skullcap, 0.05 g; *Lithospermum*, 0.1 g; *Kudingcha*, 0.05 g; Smartweed, 0.1 g; and Licorice, 0.03 g, the following results were obtained In addition, when the atopic symptoms are mild, a significant therapeutic effect can be obtained; however, when the atopic symptoms are severe, a more significant effect could be obtained by applying an atopic lotion (A, B) and/or an atopic cream (A, B), described below, developed by the applicant on the diseased part. The drinking of the drinkable tea and the applying of the atopic lotion (A, B) and/or the atopic cream (A, B) were carried out morning, noon and night.

The respective ingredients and volume ratios of atopic lotion A:

Lightyellow *Sophora* Root, 3%; Turmeric, 2%; Magnolia Bark, 2%; Moutan Bark, 2%; *Isatis* Leaf, 2%; Borneo Camphor Tree (*Dryobalanops aromatica* Gaertn. f.), 1%; Amur Cork Tree, 2%; Lemon, 3%; Smartweed, 2%; *Angelicae*

*Dahuricae* Root, 1%; Licorice, 0.5%; Cnidii Rhizoma, 0.5%; Japanese *Angelica* Root, 0.5%; salicylic acid, 0.5%; resorcinol, 0.5%; alcohol, 30%; water, 48.5%.

The respective ingredients and volume ratios of atopic lotion B:

Lightyellow *Sophora* Root, 3%; Turmeric, 2%; Magnolia Bark, 2%; Moutan Bark, 2%; *Isatis* Leaf, 1%; Borneo Camphor Tree (*Dryobalanops aromatica* Gaertn. f.), 1%; Amur Cork Tree, 2%; *Angelicae Dahuricae* Root, 1%, Lemon, 3%; Smartweed, 2%; Licorice, 0.5%; dimethylsulfoxide, 5%; salicylic acid, 0.5%; resorcinol, 0.5%; alcohol, 26%; water, 48.5%.

The respective ingredients and volume ratios of atopic cream A:

Lightyellow *Sophora* Root, 3%; Turmeric, 2%; Magnolia Bark, 2%; Moutan Bark, 2%; *Isatis* Leaf, 1%; Borneo Camphor Tree (*Dryobalanops aromatica* Gaertn. f.), 1%; Baikal Skullcap, 2%; Amur Cork Tree, 2%; *Angelicae Dahuricae* Root, 1%, Lemon, 3%; Smartweed, 2%; Licorice, 0.5%; Cnidii Rhizoma, 0.5%; Japanese *Angelica* Root, 0.5%; salicylic acid, 0.5%; resorcinol, 0.5%; mutton oil, 3%; alcohol, 3%; white soft paraffin, 70.5%.

The respective ingredients and volume ratios of atopic cream B:

Lightyellow *Sophora* Root, 3%; Turmeric, 2%; Magnolia Bark, 2%; Moutan Bark, 2%; *Isatis* Leaf, 1%; Borneo Camphor Tree (*Dryobalanops aromatica* Gaertn. f.), 1%; Baikal Skullcap, 2%; Amur Cork Tree, 2%; *Angelicae Dahuricae* Root, 1%, Lemon, 3%; Smartweed, 1%; Licorice, 0.5%; dimethylsulfoxide, 5%; salicylic acid, 0.5%; resorcinol, 0.5%; mutton oil, 3%; alcohol, 3%; white soft paraffin, 66.5%.

[CASE 1]

Patient

Distinction of sex: Female

Date of birth: Jan. 28, 1971 (Showa 46)

Age at initial consultation: 28 years old

Initial consultation: Apr. 12, 1999 (Heisei 11)

Medical history: Onset of atopy was 6 years ago. No improvement was observed after use of steroidal agent for 6 years.

Physical examination: Both hands are reddish and tumefacient; swollen.

Prescription: Drinking of 6 g per day of the drinkable tea.

Consequence: After 1 month, the effect gradually appeared; after 2 months, almost complete cure; the drinkable tea was taken 3 times a day after passage of 2 months and is now on.

Figure 1:
FIG. 1 (A) is a photograph showing the backsides of both hands when the patient in CASE 1 according to the invention has visited a doctor for initial consultation.

FIG. 1 (A) is a photograph showing the condition of the both hands at the initial consultation; FIG. 1 (B) is a photograph showing the condition of the both hands on June 21, when 2 months and 9 days were passed after starting the treatment.

[CASE 2]

Patient

Distinction of sex: Female

Date of birth: Jan. 7, 1975 (Showa 50)

Age at initial consultation: 23 years old

Initial consultation: Mar. 8, 2001 (Heisei 13)

Medical history: Onset of atopy was at about elementary school girl age. No improvement was observed on use of steroidal agent. Two years ago, aggravation was found after delivery; exanthema and flare were found on all of face, extermities and trunk.

Physical examination: Exanthema, flare, regional erosion, strong itch and burn were found on face. Skin of both hands is reddish, tumefacient and cracked. Lichenification was found locally.

Prescription: Internal: Drinking of 3 g per day of the drinkable tea.

External: Application of 3 times a day of atopic lotion A and atopic cream A on the diseased part.

Consequence: After 3 weeks, eczema, flare, erosion, cracking and so on were almost completely cured; significant inprovement of itching was found.

FIG. 2 (A) is a photograph showing the condition of the face at the initial consultation; FIG. 2 (B) is a photograph showing the condition of the face on day 13 after the treatment. FIG. 3 (A) is a photograph showing the condition of the backside of right hand at the initial consultation; FIG. 3 (B) is a photograph showing the condition of the backside of right hand on day 20 after the treatment.

[CASE 3]

Patient

Distinction of sex: Male

Date of birth: Mar. 15, 1999 (Heisei 11)

Age at initial consultation: 0 years old (24 days after birth)

Initial consultation: Apr. 8, 1999 (Heisei 11)

Medical history: Onset of eczema was 2 weeks after birth on face as main part, head, neck and round, ears, trunk and others.

Physical examination: Eczema, exanthema and swelling on face, head, neck and round; regional pus.

Prescription: Internal: Drinking of 3 g per day of the drinkable tea.

External: Application of 3 times a day of atopic lotion B and atopic cream B on diseased part.

Consequence: After 2 weeks, the skin manifestation was significantly improved, and 2 months later, the symptoms were settled and the treatment was discontinued.

FIG. 4 (A) is a photograph showing the condition of the face at the initial consultation; FIG. 4 (B) is a photograph showing the condition of the face after 2 months.

[CASE 4]

Patient

Distinction of sex: Male

Date of birth: Jan. 21, 1976 (Showa 51)

Age at initial consultation: 22 years old

Initial consultation: Dec. 11, 1998 (Heisei 10)

Medical history: Onset of atopy was at middle school boy age; gradual aggravation occurred during university student age; no improvement was observed by use of steroidal agent.

Physical examination: Flare and eczema on face and head; dry and rough. Severe eczema on both hands; strong erosion, pus, itching and burn.

Prescription: Internal: Drinking of 3 g per day of the drinkable tea.

External: Application of 3 times a day of atopic lotion B and atopic cream B on diseased part.

Consequence: after 3 weeks, eczema on both hands was almost completely cured. Improving effect was observed in symptoms on face and head.

FIG. 5 (A) is a photograph showing the condition of the fingers of the right hand at the initial consultation; FIG. 5 (B) is a photograph showing the condition of the fingers of right hand after 3 weeks.

[CASE 5]

Patient
  Distinction of sex: Female
  Date of birth: Jun. 12, 1984 (Showa 59)
  Age at initial consultation: 14 years old
Initial consultation: Dec. 20, 1998 (Heisei 10)
Medical history: Onset of atopy was found at infancy. One year ago, aggravation occurred and onset was found on all of face, trunk and extremities; erosion and pus were found. Particularly, exanthema on gluteal region and both lower limb was severe and there is a strong itching and burn.
Prescription: Internal: Drinking of 3 g per day of the drinkable tea.
External: Application of 3 times a day of atopic lotion A and atopic cream A on diseased part.

Consequence: After 2 weeks, improvement of symptoms was found. Crack on sole of right foot was completely cured. Afterwards, only the drinking of the drinkable tea was continued, and the course is i good order.

FIG. 6 (A) is a photograph showing the condition of the sole of right foot at the initial consultation; FIG. 6 (B) is a photograph showing the condition of the sole of right foot after 3 weeks.

[CASE 6]

Patient
  Distinction of sex: Male
  Date of birth: Dec. 11, 1980 (Showa 55)
  Age at initial consultation: 20 years old
Initial consultation: Apr. 1, 1999 (Heisei 11)
Medical history: Onset of atopy was after birth; steroid therapy was attempted at elementary to middle school boy age but no effect was found and the therapy was discontinued. Thereafter, antihistaminic agent alone was taken.
Physical examination: exanthema, dark redness and pigmentation on face; red swelling on neck, trunk and joints in extremeties; many exfoliation; lichenification was found locally; itching is strong.
Prescription: Internal: Drinking of 3 g per day of the drinkable tea.
External: Application of 3 times a day of atopic lotion B and atopic cream A on diseased part. Consequence: After 2 months, eczema, dark redness and pigmentation on face were almost completely cured. Eczema on trunk and extremities were significantly improved and the course afterwards is in good order.

FIG. 7 (A) is a photograph showing the condition of the face at the initial consultation; FIG. 7 (B) is a photograph showing the condition of the face after 2 months.

As described above, the drinkable tea for therapy of dermatitis according to the invention can improve the physical constitution from inside of the body as compared with the external medicines; as shown in CASE 1, an excellent therapeutic effect can be obtained by only drinking of the drinkable tea; as shown in CASE 2 to CASE 6, a significant therapeutic effect owing to the improvement of physical constitution from the inside of the body and a symptomatic therapeutic effect in diseased part with the external medicine when an external medicine such as atopic lotion (A, B) and/or atopic cream (A, B) is applied in the initial stage of the therapy or during the total period of the therapy.

The invention claimed is:

1. A tea composition for treating dermatitis, comprising: extracts obtained from lightyellow Sophora root (*Sophora flavescens* Ait.), isatis leaf (*Isatis tinctoria* L.), and at least one auxiliary material containing extracts obtained from one, or more medicinal herbs selected from the group consisting of Japanese Angelica root (*Angelica sinensis* (olive) Diels.), oldenlandia diffusa (*Oldenlandia diffusa* Roxb.), smilax glabra (*Smilax glabra* Roxb.), dried tangerine peel (*Citrus reticulate* Blanco.), wild chrysanthemum flower (*Chrysanthemum indicum* L.), corydalis (*Corydalis bulosa* DC.), peppermint (*Menthe arvensis* L.), baikal skullcap (*Scutellaria baicalensis* Georgi.), lithospermum (*Lithospermum erythrohizon* Sieb. et Zucc.), Kudingcha (*Kudingeha*), smartweed (*Polygonum cuspidatum* Sicb. et Zucc.), and licorice (*Glycyrrhiza uralensis* Fisch.),
  wherein the weights of extract ingredients obtained from respective medicinal herbs per gram (g) of tea are: lightyellow *Sophora* root, 0.09 to 0.11 g; and *isatis* leaf, 0.09 to 0.11 g; and the weights of said auxiliary material are: Japanese *Angelica* root, 0.045 to 0.055 g; oldenlandia diffusa, 0.09 to 0.11 g; *smilax glabra*, 0.108 to 0.132 g; dried tangerine peel, 0.045 to 0.055 g; wild chrysanthemum flower, 0.09 to 0.11 g; *corydalis*, 0.018 to 0.022 g; peppermint, 0.09 to 0.11 g; baikal skullcap, 0.045 to 0.055 g; *lithospermum*, 0.009 to 0.011 g; *kudingcha*, 0.045 to 0.055 g; smartweed, 0.09 to 0.11 g; and licorice, 0.027 to 0.033 g.

2. The tea composition for treating dermatitis according to claim 1, wherein said tea is in the form of a liquid.

3. The tea composition for treating dermatitis according to claim 1, wherein said tea is in the form of a powder or granule.

4. The tea composition for treating dermatitis according to claim 1, wherein the weights of extract ingredients obtained from respective medicinal herbs per gram (g) of tea are: lightyellow *Sophora* root, 0.1 g; and *isatis* leaf, 0.1 g; and the weights of said auxiliary material are: Japanese *Angelica* root, 0.05g; *oldenlandia diffusa*, 0.1 g; *smilax glabra*, 0.12 g; dried tangerine peel, 0.05 g; wild chrysanthemum flower, 0.1 g; *corydalis*, 0.02 g; peppermint, 0.01 g; baikal skullcap, 0.05g; *lithospermum*, 0.1 g; *kudingcha*, 0.05 g grams; smartweed, 0. 1 g; and licorice, 0.03 g.

* * * * *